(12) United States Patent
Nakano et al.

(10) Patent No.: US 9,772,293 B2
(45) Date of Patent: Sep. 26, 2017

(54) APPARATUS FOR MEASURING PARTIAL PRESSURE OF CARBON DIOXIDE AND CELL UNIT FOR THE APPARATUS

(71) Applicant: Japan Agency for Marine-Earth Science and Technology, Yokosuka-shi, Kanagawa (JP)

(72) Inventors: Yoshiyuki Nakano, Kanagawa (JP); Hideshi Kimoto, Osaka (JP); Takahiko Suzue, Osaka (JP); Shuji Murata, Osaka (JP)

(73) Assignee: JAPAN AGENCY FOR MARINE-EARTH SCIENCE AND TECHNOLOGY, Yokosuka-Shi (JP)

( * ) Notice: Subject to any disclaimer, the term of this patent is extended or adjusted under 35 U.S.C. 154(b) by 155 days.

(21) Appl. No.: 14/655,129

(22) PCT Filed: Dec. 25, 2013

(86) PCT No.: PCT/JP2013/084743
§ 371 (c)(1),
(2) Date: Jun. 24, 2015

(87) PCT Pub. No.: WO2014/104128
PCT Pub. Date: Jul. 3, 2014

(65) Prior Publication Data
US 2015/0323468 A1    Nov. 12, 2015

(30) Foreign Application Priority Data
Dec. 25, 2012 (JP) .................... 2012-281553

(51) Int. Cl.
*G01N 21/78* (2006.01)
*G01L 11/02* (2006.01)
(Continued)

(52) U.S. Cl.
CPC ............. *G01N 21/78* (2013.01); *G01L 11/02* (2013.01); *G01N 21/0317* (2013.01);
(Continued)

(58) Field of Classification Search
CPC ............... G01N 21/78; G01N 21/3504; G01N 21/0317; G01N 33/182; G01L 11/02
See application file for complete search history.

(56) References Cited

U.S. PATENT DOCUMENTS

2010/0240141 A1  9/2010  Nakano
2010/0269940 A1  10/2010  Wynn et al.

FOREIGN PATENT DOCUMENTS

| JP | 1-22112 | 6/1989 |
| JP | 2004-294355 | 10/2004 |
| JP | 2009-198488 | 9/2009 |

OTHER PUBLICATIONS

Michael D. DeGrandpre and Matthew M. Baehr: "Calibration-Free Optical Chemical Sensors". Analytical Chemistry, 71, 1152 (1999), Discussed in specification, English text.
(Continued)

*Primary Examiner* — Jill Warden
*Assistant Examiner* — Matthew Krcha
(74) *Attorney, Agent, or Firm* — Rankin, Hill & Clark LLP

(57) ABSTRACT

An apparatus for accurately measuring carbon dioxide partial pressure even if the apparatus is disposed in an environment at a high ambient water pressure, such as in a deep sea environment. A through hole that penetrates a body portion is formed in the body portion. The body portion is connected to a light source unit and a light receiving element unit. A signal line is disposed to pass through the through hole formed in the body portion. The signal line electrically connects between an amplifier substrate of the light receiving element unit and a CPU substrate of the light source unit to transfer the detection result amplified by the amplifier substrate.

21 Claims, 8 Drawing Sheets

(51) Int. Cl.
*G01N 21/3504* (2014.01)
*G01N 21/03* (2006.01)
*G01N 33/18* (2006.01)
*G01N 21/80* (2006.01)

(52) U.S. Cl.
CPC ....... *G01N 21/3504* (2013.01); *G01N 33/182* (2013.01); *G01N 21/80* (2013.01); *G01N 2201/0218* (2013.01); *G01N 2201/062* (2013.01); *G01N 2201/0627* (2013.01)

(56) References Cited

OTHER PUBLICATIONS

"Stimultaneous Vertical Measurements of In Situ pH and C02 in the Sea Using Spectrophotometric Profilers", Journal of Oceanography, vol. 62, No. 1, Feb. 2006, pp. 71-81 *Figure 2, Listed in International Search Report, English text.
Nakano, Y.: "pH-C02 Hybrid Sensor no Kaihatsu" (translated as "Development of in situ C02 and pH sensor"), Engineering Materials; ISSN: 0452-2834, vol. 61, No. 7, Jul. 1, 2013, pp. 77-80 *Figures 1-2<Non-patent document>: Brief Description prepared in English is attached; Excerpt page (Fig.2) translated into English is attached, Listed in International Search Report.
International Search Report, Date of mailing: Feb. 10, 2014 (Feb. 10, 2014).

Fig.10

| ZONE | OCEAN | | $NA_T (\mu mol/kg)$ |
|---|---|---|---|
| 1 | ATLANTIC OCEAN INDIAN OCEAN | EQUATORIAL AREA AND MID-LATITUDE AREA (30°S -30°N, t>20°C) EQUATORIAL AREA, SUBTROPIC AREA, AND ARABIAN SEA (25°S-30°N, t>20°C) | 2291 |
| 2 | ATLANTIC OCEAN | NORTH ATLANTIC AREA (30°N-80°N, 0>t>20°C) | $2291-2.69(t-20)-0.046(t-20)^2$ |
| 3 | PACIFIC OCEAN PACIFIC OCEAN | EQUATORIAL AREA (UPWELLING AREA) (75-110°W →20°N-20°S) PACIFIC OCEAN (110-140°W →10°N-10°S), 20<t<29°C | $2300-2.94(t-29)-0.058(t-29)^2$ |
| 4 | PACIFIC OCEAN | SEA CURRENTS (NORTH AND SOUTH) (20°S-30°N) | 2300 |
| 5 | PACIFIC OCEAN | NORTH LATITUDE AREA | $2300-7.00(t-20)-0.158(t-20)^2$ |
| 6 | ANTARCTIC SEA | (30°S-70°S, -1<t<20°C) | $A-2.52(t-20)+0.056(t-20)^2$ |

A=2300; PACIFIC OCEAN
A=2291; PACIFIC OCEAN AND INDIAN OCEAN

APPARATUS FOR MEASURING PARTIAL PRESSURE OF CARBON DIOXIDE AND CELL UNIT FOR THE APPARATUS

TECHNICAL FIELD

The present invention relates to an apparatus for measuring the partial pressure of carbon dioxide and a cell unit for the apparatus.

BACKGROUND ART

In recent years, the mechanism of carbon cycling in an ocean has been progressively clarified in association with global warming. It is known that in the carbonic acid system in the ocean, if two out of four items consisting of the alkalinity of sea water ($A_T$: the difference between the total charge concentration of positive ions in sea water and the total charge concentration of negative ions in sea water), the total carbonic acid concentration ($C_T$: total dissolved inorganic carbon), the carbon dioxide partial pressure $pCO_2$, and the hydrogen ion concentration pH are measured, the remaining items can be calculated. Lately, in particular, it has been desired to measure the carbon dioxide partial pressure in deep sea in order to clarify the carbon cycling mechanism in detail. Non-Patent Document 1 discloses an apparatus for measuring the partial pressure of carbon dioxide according to the related art that can measure $pCO_2$ in deep sea.

RELATED-ART DOCUMENT

Non-Patent Document

[Non-Patent Document 1] Michael D. DeGrandpre and Matthew M. Baehr (1999) Calibration-Free Optical Chemical Sensors, Analytical Chemistry, 71, 1152

SUMMARY OF INVENTION

Technical Problem

In the apparatus for measuring the partial pressure of carbon dioxide ($pCO_2$) according to Non-Patent Document 1, a gas permeable membrane is used to equilibrate the partial pressure of carbon dioxide in sampled sea water with the partial pressure of carbon dioxide in a reagent solution that flows inside the gas permeable membrane, a pH indicator contained in the reagent solution is discolored so that the discolored reagent solution is introduced into a flow cell, which is irradiated with light from a light source so that light having passed through the reagent solution is received by a light receiving element, and the carbon dioxide partial pressure is measured from variations in absorbance of the reagent solution. In the conventional apparatus described in Non-Patent Document 1, however, a lead wire that electrically connects between the light source and the light receiving element is exposed to the sea. Therefore, if the apparatus is disposed in deep sea, for example, to measure the carbon dioxide partial pressure in deep sea, the lead wire may be damaged by an external force, and it is necessary to adopt a strict watertight structure at a portion at which the lead wire is led out. In the conventional apparatus described in Non-Patent Document 1, further, light from the light source in a pressure-proof container is introduced into the flow cell to be irradiated to the reagent solution via an optical fiber located in water, and light output from the cell is led to the light receiving element in the pressure-proof container again via another optical fiber. The optical fibers located in water may be affected by the ambient pressure, and may be affected by vibration and a water flow. If the optical fibers are vibrated even only slightly, noise or a drift is generated, which affects the amount of light to be propagated to cause an error. This finally makes it impossible to accurately measure the carbon dioxide partial pressure.

An object of the present invention is to provide an apparatus for measuring the partial pressure of carbon dioxide that can accurately measure the carbon dioxide partial pressure and that is unlikely to be broken even if the apparatus is disposed in an environment at a high ambient water pressure such as deep sea.

Solution to Problem

The present invention improves an apparatus for measuring the partial pressure of carbon dioxide, the apparatus being disposed underwater and including an equilibrator, a liquid feed pump, a flow cell, a light source unit, a light receiving element unit, and a carbon dioxide partial pressure measuring section. The equilibrator equilibrates the partial pressure of carbon dioxide in a reagent solution and the partial pressure of carbon dioxide in sample water. The equilibrator includes a solution flow passage through which the reagent solution flows, the reagent solution having an absorbance varying with the partial pressure of carbon dioxide, and a gas permeable membrane that allows permeation of carbon dioxide but that does not allow permeation of a solution. The equilibrator equilibrates the partial pressure of carbon dioxide via the gas permeable membrane without mixing the reagent solution and the sample water. The liquid feed pump feeds the reagent solution to the solution flow passage. The flow cell has a body portion formed with an inside flow passage through which the reagent solution flowing out of the solution flow passage of the equilibrator flows. The light source unit irradiates light to the inside flow passage. The light receiving element unit includes a light receiving element configured to receive the light having passed through the inside flow passage. In the apparatus according to the present invention, in particular, the body portion of the flow cell has a watertight structure in which the inside flow passage includes a first opening portion watertightly blocked by a first optical window and a second opening portion located opposite to the first opening portion and watertightly blocked by a second optical window. The light source unit includes a watertight first container watertightly attached to the body portion of the flow cell, and is configured to irradiate the light from a light source to the inside flow passage through the first optical window. The light receiving element unit includes a watertight second container watertightly attached to the body portion of the flow cell, and is configured such that the light receiving element receives the light having passed through the inside flow passage through the second optical window. The body portion of the flow cell is formed with an electrical connection member guide passage to allow passage of an electrical connection member, such as a lead wire, used for electrical connection between the light source unit and the light receiving element unit. The electrical connection member such as a lead wire as used herein includes a so-called wire harness formed by bundling a plurality of lead wires including a connector. According to the present invention, the electrical connection member such as a lead wire used to electrically connect between the light source unit and the light receiving element unit is disposed in a watertight structure formed from the flow cell, the light source unit, and the light receiving element unit when the light source unit and the light receiving element unit are water-tightly attached to the flow cell. Thus, the electrical connection member such as a lead wire is not exposed to water in which the apparatus is disposed. Thus, the apparatus is hardly broken because of a bad connection, a water leak, or the like. Moreover, it is possible to reduce the number of locations at which a watertight structure is to be adopted. In addition, the flow cell and the first container and the second container having a watertight structure are watertightly attached to each other. Thus, water around the apparatus does not enter the apparatus. Therefore, no optical fibers are required. In addition, the electrical connection member and a light conducting passage are not affected by the water pressure of water in which the apparatus is disposed. Thus, an electric signal and an optical signal transferred between the light source unit and the light receiving element unit are not affected by the water pressure, and a measurement error of the carbon dioxide partial pressure or the like is not caused. Hence, according to the present invention, the carbon dioxide partial pressure can be accurately measured even if the apparatus is disposed in deep sea in which the water pressure is high, for example.

The apparatus may further include a sampling pump configured to sample the sample water from the underwater, and a pump drive device configured to control drive of the sampling pump. In this case, the equilibrator further includes a sample water flow passage through which the sample water passes. With such a configuration, the sample water having flowed into the sample water flow passage of the equilibrator can be caused to reside in the sample water flow passage by stopping drive of the sampling pump. Therefore, the partial pressure of carbon dioxide $pCO_2$ in the sampled sample water and the partial pressure of carbon dioxide $pCO_2$ in the inside liquid can be sufficiently equilibrated, which makes it possible to measure the carbon dioxide partial pressure with high accuracy. In addition, the sample water can be positively caused to flow into the sample water flow passage by driving the sampling pump, which makes it possible to accurately measure the partial pressure of carbon dioxide in the desired sample water.

The apparatus may further include a pH meter configured to measure the pH of the sample water. In this case, the pump drive device is configured to stop drive of the sampling pump until the carbon dioxide partial pressure measuring section completes the measurement when the pH meter measures a pH value that is equal to or more than a prescribed pH value. With such a configuration, it is possible to presume whether or not sample water possibly containing carbon dioxide is sampled based on the pH value measured by the pH meter. When the pH meter measures a pH value that is equal to or more than a prescribed pH value and it is presumed that sample water possibly containing carbon dioxide is sampled, drive of the sampling pump is stopped until the carbon dioxide partial pressure measuring section completes the measurement. As a result, the sampled sample water is not discharged from the equilibrator, which makes it possible to reliably establish an equilibrium state between the partial pressure of carbon dioxide in the reagent solution and the partial pressure of carbon dioxide in the sampled sample water.

The body portion of the flow cell may include an inlet port constituted by one end of the inside flow passage and an outlet port constituted by the other end of the inside flow passage, for example. In this case, the inlet port and the outlet port are formed in a pair of opposed outer wall surfaces of the body portion, respectively. The light source unit and the light receiving element unit are attached to the body portion at another pair of outer wall surfaces of the body portion that serve as attachment surfaces and that are different from the pair of outer wall surfaces in which the inlet port and the outlet port are formed. With such a configuration, the light source unit, the flow cell, and the light receiving element unit are sequentially disposed in order such that light can be irradiated to the inside flow passage and the light having passed through the inside flow passage can be received by the light receiving element, which simplifies the configuration of the apparatus. The inlet port and the outlet port may be formed in the same surface of the body portion of the flow cell. With this configuration, the solution flow passage and the inside flow passage can be easily connected from the same side.

Preferably, the reagent solution is a pH-sensitive colorimetric reagent having a pH of 5.5 to 6. The time required for carbon dioxide to be hydrated into carbonic acid ($CO_2 + H_2O \rightarrow H_2CO_3$) and for carbonic acid to be dissociated into hydrogen carbonate ions ($H_2CO_3 \rightarrow H^+ + HCO_3^-$) to reach an equilibrium is shorter to provide a quicker response on the acidic side around a pH of 5 than at a pH of 8. When the pH of the reagent solution is 5.5 to 6, the time for carbonic acid to be dissociated into hydrogen carbonate ions to reach an equilibrium of carbonic acid can be made shorter than when the pH is 6.5 or more, which makes it possible to quickly measure the carbon dioxide partial pressure. When the pH of the reagent solution is less than 5.5, an equilibrium of carbonic acid can be reached quickly, but dissociation occurs to reduce the amount of hydrogen carbonate ions, which reduces variations in hydrogen ion concentration. When the pH of the reagent solution is more than 6, a long time is required to reach an equilibrium of carbonic acid. Particularly preferably, the pH-sensitive colorimetric reagent is a sulfonephthalein pH indicator.

Preferably, the apparatus further includes a salinity sensor configured to measure the salinity of the sample water, and a temperature sensor configured to measure the temperature of the sample water. In this case, the apparatus further includes a total alkalinity computing section configured to compute a total alkalinity based on the measured salinity and temperature, and a carbon dioxide partial pressure estimating section configured to compute the partial pressure of carbon dioxide based on the computed total alkalinity and the pH value of the water. The pump drive device drives the sampling pump based on the partial pressure of carbon dioxide computed by the carbon dioxide partial pressure estimating section. With such a configuration, the time required to sufficiently equilibrate the partial pressure of carbon dioxide $pCO_2$ in the sampled sample water and the partial pressure of carbon dioxide $pCO_2$ in the inside liquid can be calculated based on the estimated carbon dioxide partial pressure, and the time for driving the sampling pump can be set based on the calculated time.

Preferably, the flow cell, the watertight first container, and the watertight second container have a pressure-proof structure. With such a configuration, it is no longer necessary to dispose the apparatus in another pressure-proof container or the like, which makes it possible to directly dispose the apparatus in water at a high water pressure such as deep sea.

The present invention can be implemented as a cell unit for an apparatus for measuring the partial pressure of carbon dioxide.

BRIEF DESCRIPTION OF DRAWINGS

FIG. 10 is a table illustrating an example of expressions for calculating $NA_T$ for sea areas of each ocean.

DESCRIPTION OF EMBODIMENTS

Figure 1:
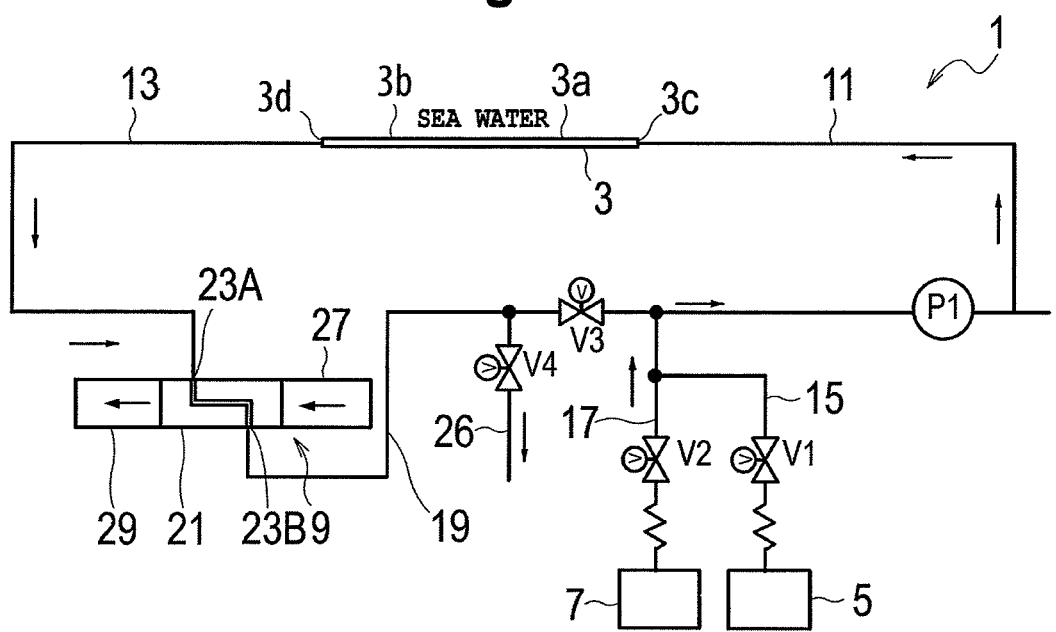
FIG. 1 schematically illustrates the configuration of an apparatus for measuring the partial pressure of carbon dioxide according to a first embodiment of the present invention.

Embodiments of the present invention will be described below with reference to the drawings. FIG. 1 schematically illustrates the configuration of an apparatus for measuring the partial pressure of carbon dioxide according to a first embodiment of the present invention. As illustrated in FIG. 1, an apparatus for measuring the partial pressure of carbon dioxide 1 according to the embodiment includes an equilibrator 3, a reagent container 5 filled with a reagent solution, a pure water container 7 filled with pure water, a cell unit 9, and an inside liquid feed pump P1. The apparatus 1 is disposed in sea water by being attached to a floating structure having a buoy configured to float on the sea or inside a mobile body such as an AUV (autonomous underwater vehicle), an ROV (remotely operated vehicle), and a manned underwater vehicle, by being towed by a research ship together with a water sampler, or the like. The apparatus 1 according to the embodiment navigates deep sea together with an underwater vehicle such as an AUV (not illustrated) configured to navigate deep sea, or is towed by a research ship.

The equilibrator 3 includes a hollow cylindrical tubular member 3a formed from a porous gas permeable membrane. An inside liquid flow passage 3b is formed by a hollow portion of the tubular member 3a. The gas permeable membrane according to the embodiment is formed from an amorphous fluoropolymer with an inside diameter of 1 mm. The gas permeable membrane may be formed from polytetrafluoroethylene or silicon. The gas permeable membrane is a porous membrane formed with a multiplicity of extremely fine pores, and does not allow permeation of a liquid but allows permeation of a gas component such as carbon dioxide contained in the liquid. The tubular member 3a formed from the gas permeable membrane is flexible, and formed to have a length of 1000 mm. In practice, the tubular member 3a according to the embodiment is formed in a coil shape by being wound around a fixation jig configured to fix the gas permeable membrane while allowing a flow of sea water. One end portion 3c of the tubular member 3a is connected to the inside liquid feed pump P1 via a first liquid feed conduit 11 that is made of polytetrafluoroethylene and that supplies an inside liquid, carbon dioxide contained in which is to be measured, to the inside of the inside liquid flow passage 3b. The other end portion 3d of the tubular member 3a is connected to the cell unit 9 via a second liquid feed conduit 13 that is made of polytetrafluoroethylene and that discharges the inside liquid from the inside of the inside liquid flow passage 3b. The equilibrator 3 according to the embodiment is directly disposed in sea water, and a flow of sea water is formed around the tubular member 3a of the equilibrator 3 by a sea current or navigation of the AUV.

The reagent container 5 stores bromocresol purple (BCP), which is a pH-sensitive colorimetric indicator and a sulfonephthalein pH indicator, as the reagent solution. Examples of the reagent solution include bromophenol blue, metacresol purple, methyl red, phenol red, and thymol blue. The pH of the reagent formed from BCP is adjusted to 5.5 to 6.0. A third liquid feed conduit 15 made of polytetrafluoroethylene and merged with a fifth liquid feed conduit 19 to be discussed later is connected to the reagent container 5. The reagent container 5 is connected to the inside liquid feed pump P1 via the third liquid feed conduit 15 and the fifth liquid feed conduit 19. The reagent stored in the reagent container 5 is fed to the equilibrator 3 and the cell unit 9 by driving the inside liquid feed pump P1 with a valve V1 provided in the third liquid feed conduit 15 open.

The pure water container 7 stores pure water. A fourth liquid feed conduit 17 made of polytetrafluoroethylene and merged with the third liquid feed conduit 15 is connected to the pure water container 7. The pure water container 7 is connected to the inside liquid feed pump P1 via the fourth liquid feed conduit 17, the third liquid feed conduit 15, and the fifth liquid feed conduit 19. The pure water stored in the pure water container 7 is fed to the equilibrator 3 and the cell unit 9 by driving the inside liquid feed pump P1 with a valve V2 provided in the fourth liquid feed conduit 17 open.

Figure 2A:
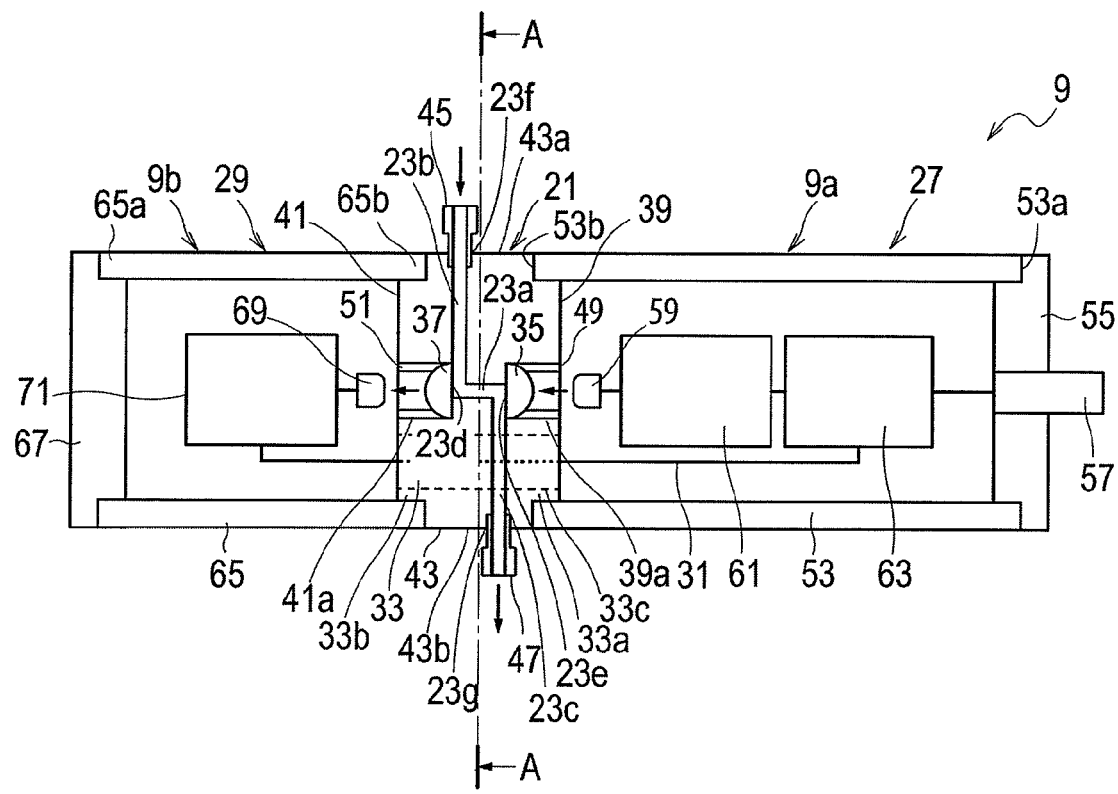
FIG. 2A schematically illustrates the configuration of a cell unit according to the first embodiment.
Figure 2B:
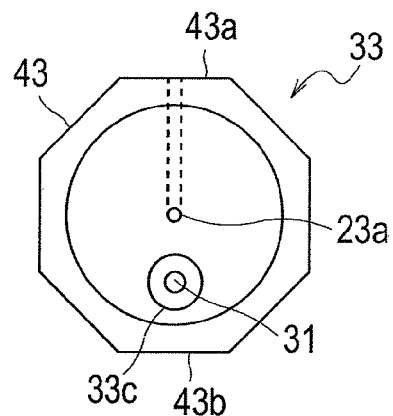
FIG. 2B is an end surface cross-sectional view taken along the line A-A of FIG. 2A.

The cell unit 9 includes a flow cell 21, a light source unit 27, a light receiving element unit 29, and a signal line 31 formed from an electrical connection member such as a lead wire illustrated in FIG. 2B. An inside flow passage 23 is formed in the flow cell 21. The second liquid feed conduit 13 is connected to one end portion 23A of the inside flow passage 23. The fifth liquid feed conduit 19, which is connected to the inside liquid feed pump P1, is connected to the other end portion 23B of the inside flow passage 23. The inside liquid supplied to the inside flow passage 23 is circulated to and from the equilibrator 3 by driving the inside liquid feed pump P1 with a valve V3 provided in the fifth liquid feed conduit 19 open. The circulation of the inside liquid is stopped by closing the valve V3.

A waste liquid conduit 26 is branched from the fifth liquid feed conduit 19. The inside liquid supplied to the inside flow passage 23 is discharged to the outside from the waste liquid conduit 26 when the inside liquid feed pump P1 is driven with the valve V3 closed and a valve V4 provided in the waste liquid conduit 26 open.

FIG. 2A is a schematic vertical sectional view illustrating the configuration of the cell unit 9 according to the embodiment. FIG. 2B is an end surface cross-sectional view taken along the line A-A of FIG. 2A. Cross sections are not hatched in the drawings.

The flow cell 21 includes a body portion 33 formed with the inside flow passage 23, a light source pressure-proof lens 35, and a light receiving element pressure-proof lens 37.

The body portion 33 is formed from polyether ether ketone (PEEK), and includes a first outer wall surface 39 that opposes the light source unit 27, a second outer wall surface 41 that opposes the light receiving element unit 29, and a peripheral wall surface 43 that connects between the first outer wall surface 39 and the second outer wall surface 41. The body portion 33 may be made of rigid vinyl chloride or any other material that can be lathed and that is not easily deteriorated or deformed by sea water at a high pressure. The body portion 33 has a generally regular octagonal cross-sectional shape. The first outer wall surface 39 and the second outer wall surface 41 have a circular shape. The body portion may have a circular or regular square cross-sectional shape.

The body portion 33 has annular stepped portions 33a and 33b formed at an edge portion of the peripheral wall surface 43 on the first outer wall surface 39 side and an edge portion of the peripheral wall surface 43 on the second outer wall surface 41 side, respectively. An end portion 65b of a second cylinder 65 of a first container 9a of the light source unit 27 is screwed to the annular stepped portion 33a. An end portion 53b of a first cylinder 53 of a second container 9b of the light receiving element unit 29 is screwed to the annular stepped portion 33b. Thus, threads (not illustrated) are formed on the outer peripheral portion of the annular stepped portions 33a and 33b and the inner peripheral portion of the end portion 65b of the second cylinder 65 and the end portion 53b of the first cylinder 53.

The body portion 33 also has a through hole 33c formed to penetrate the body portion 33 and open in the first outer wall surface 39 and the second outer wall surface 41. The signal line 31 to be discussed later is inserted into the through hole 33c.

The inside flow passage 23 formed in the body portion 33 includes a light irradiation portion 23a configured to extend in the direction of coupling between the light source unit 27 and the light receiving element unit 29, an introduction passage portion 23b configured to introduce the inside liquid into the light irradiation portion 23a, and a discharge passage portion 23c configured to discharge the inside liquid from the light irradiation portion 23a. The introduction passage portion 23b has an opening portion 23d that opens in a recessed portion 39a formed in the first outer wall surface 39 to be discussed later. The discharge passage portion 23c has an opening portion 23e that opens in a recessed portion 41a formed in the second outer wall surface 41 to be discussed later. Respective end portions of the introduction passage portion 23b and the discharge passage portion 23c that are not connected to the light irradiation portion 23a open in a pair of opposed peripheral wall surfaces 43a and 43b of the body portion 33 to form an inlet port 23f and an outlet port 23g, respectively. The inlet port 23f is provided with a solution inlet joint 45 to be connected to the second liquid feed conduit 13. The outlet port 23g is provided with a solution outlet joint 47 to be connected to the fifth liquid feed conduit 19.

The recessed portion 39a which has a circular column shape is formed in the first outer wall surface 39. The recessed portion 39a communicates with the inside flow passage 23 via the opening portion 23e of the discharge passage portion 23c. The light source pressure-proof lens 35 is set at the bottom portion of the recessed portion 39a. A watertight structure is formed by an O-ring (not illustrated) between the lens 35 and the bottom portion of the recessed portion 39a. The light source pressure-proof lens 35 is pressed against the bottom portion of the recessed portion 39a by a cylindrical light source lens pusher 49 provided along the inner peripheral wall of the recessed portion 39a to watertightly block the opening portion 23e of the discharge passage portion 23c. In the embodiment, the light source pressure-proof lens 35 forms an optical window.

The recessed portion 41a which has a circular column shape is formed in the second outer wall surface 41. The recessed portion 41a communicates with the inside flow passage 23 via the opening portion 23d of the introduction passage portion 23b. The light receiving element pressure-proof lens 37 is set at the bottom portion of the recessed portion 41a. The light receiving element pressure-proof lens 37 is pressed against the bottom portion of the recessed portion 41a by a cylindrical light receiving lens pusher 51 provided along the peripheral wall of the recessed portion 41a to watertightly block the opening portion 23d of the introduction passage portion 23b. In the embodiment, the light receiving element pressure-proof lens 37 forms an optical window.

The light source unit 27 includes the first cylinder 53, a first end bracket 55, an underwater connector 57, an LED unit 59, a control substrate 61, and a CPU substrate 63. In the embodiment, the first cylinder 53 and the first end bracket 55 form the first container 9a. The first cylinder 53 is formed in a cylindrical shape from a material having water-proof and pressure-proof functions such as an aluminum material. The first end bracket 55 is set at one end portion 53a of the first cylinder 53 in the axial direction. The first end bracket 55 is formed from an aluminum material or the like. A watertight structure is formed by an O-ring (not illustrated) between the cylinder 53 and the first end bracket 55. The underwater connector 57 is provided at the center of the first end bracket 55. An external output signal line (not illustrated) configured to output the carbon dioxide partial pressure measurement result to the outside is connected to the underwater connector 57. The first end bracket 55 is screwed into the first cylinder 53 with an O-ring (not illustrated) provided therebetween to provide a watertight structure.

The first cylinder 53 has a threaded portion (not illustrated) formed on the inner wall surface of an edge portion of the first cylinder 53 on the other end portion 53b side in the axial direction to be screwed into a threaded portion formed on the surface of the stepped portion 33a of the body portion 33. In addition, an O-ring (not illustrated) is provided between the inner wall surface of the edge portion of the first cylinder 53 on the other end portion 53b side and the surface of the stepped portion 33a of the body portion 33. The first cylinder 53 and the body portion 33 are watertightly connected to each other by rotating the first end bracket 55 when the stepped portion 33a of the body portion 33 is disposed in the other end portion 53b of the first end bracket 55 in the axial direction.

The LED unit 59 has a plurality of LEDs (light emitting diodes) configured to emit light at different wavelengths, and causes the plurality of LEDs to emit light according to an output from the control substrate 61. The plurality of LEDs are disposed to oppose the light source pressure-proof lens 35 when the light source unit 27 is connected to the body portion 33 to irradiate light to the inside liquid in the light irradiation portion 23a of the inside flow passage 23. The control substrate 61 outputs a control signal for controlling drive of the plurality of LEDs to the LED unit based on an output from the CPU substrate 63.

The CPU substrate 63 includes a microcomputer integrating a central processing unit (CPU) and a memory mounted thereon. The memory stores in advance absorbance information (i.e. calibration curve information) on the inside liquid for various values of the carbon dioxide partial pressure and the temperature. The CPU computes the carbon dioxide partial pressure measurement result based on an output from the light receiving element unit 29 and the absorbance information stored in the memory, and outputs the computation result from the underwater connector 57. In the embodiment, the CPU substrate 63 forms a carbon dioxide partial pressure measuring section.

The light receiving element unit 29 includes the second cylinder 65, a second end bracket 67, a light receiving sensor 69, and an amplifier substrate 71.

In the embodiment, the second cylinder 65 and the second end bracket 67 form the second container 9b. As with the first cylinder 53, the second cylinder 65 is formed in a cylindrical shape from a material having water-proof and pressure-proof functions such as an aluminum material. The second end bracket 67 which is formed from an aluminum material or the like is fitted to one end portion 65a of the second cylinder 65 in the axial direction. The second end bracket 67 is screwed into the second cylinder 65 with an O-ring (not illustrated) provided therebetween to provide a watertight structure.

The second cylinder 65 has a threaded portion (not illustrated) formed on the inner wall surface of an edge portion of the second cylinder 65 on the other end portion 65b side in the axial direction to be screwed into a threaded portion formed on the surface of the stepped portion 33b of the body portion 33. In addition, an O-ring (not illustrated) is provided between the inner wall surface of the edge portion of the second cylinder 65 on the other end portion 65b side and the surface of the stepped portion 33b of the body portion 33. The second cylinder 65 and the body portion 33 are watertightly connected to each other by rotating the second end bracket 67 when the stepped portion 33b of the body portion 33 is disposed in the other end portion 65b of the second end bracket 67 in the axial direction.

The light receiving sensor 69 is disposed to oppose the light receiving element pressure-proof lens 37 when the light receiving element unit 29 is connected to the body portion 33 to receive light having passed through the inside liquid in the light irradiation portion 23a of the inside flow passage 23. The light receiving sensor 69 receives light having passed through the inside liquid in the light irradiation portion 23a of the inside flow passage 23 to measure the absorbance of the inside liquid to output a signal for the measurement result to the amplifier substrate 71. The amplifier substrate 71 amplifies the signal for the measurement result output from the light receiving sensor 69 to output the amplified signal to the CPU substrate 63 of the light source unit 27 via the signal line 31.

The signal line 31 electrically connects between the amplifier substrate 71 of the light receiving element unit 29 and the CPU substrate 63 of the light source unit 27, and outputs the signal for the detection result amplified by the amplifier substrate 71 to the CPU substrate 63. The signal line 31 passes through the through hole 33c formed in the body portion 33 to electrically connect between the amplifier substrate 71 and the CPU substrate 63.

Figure 3:
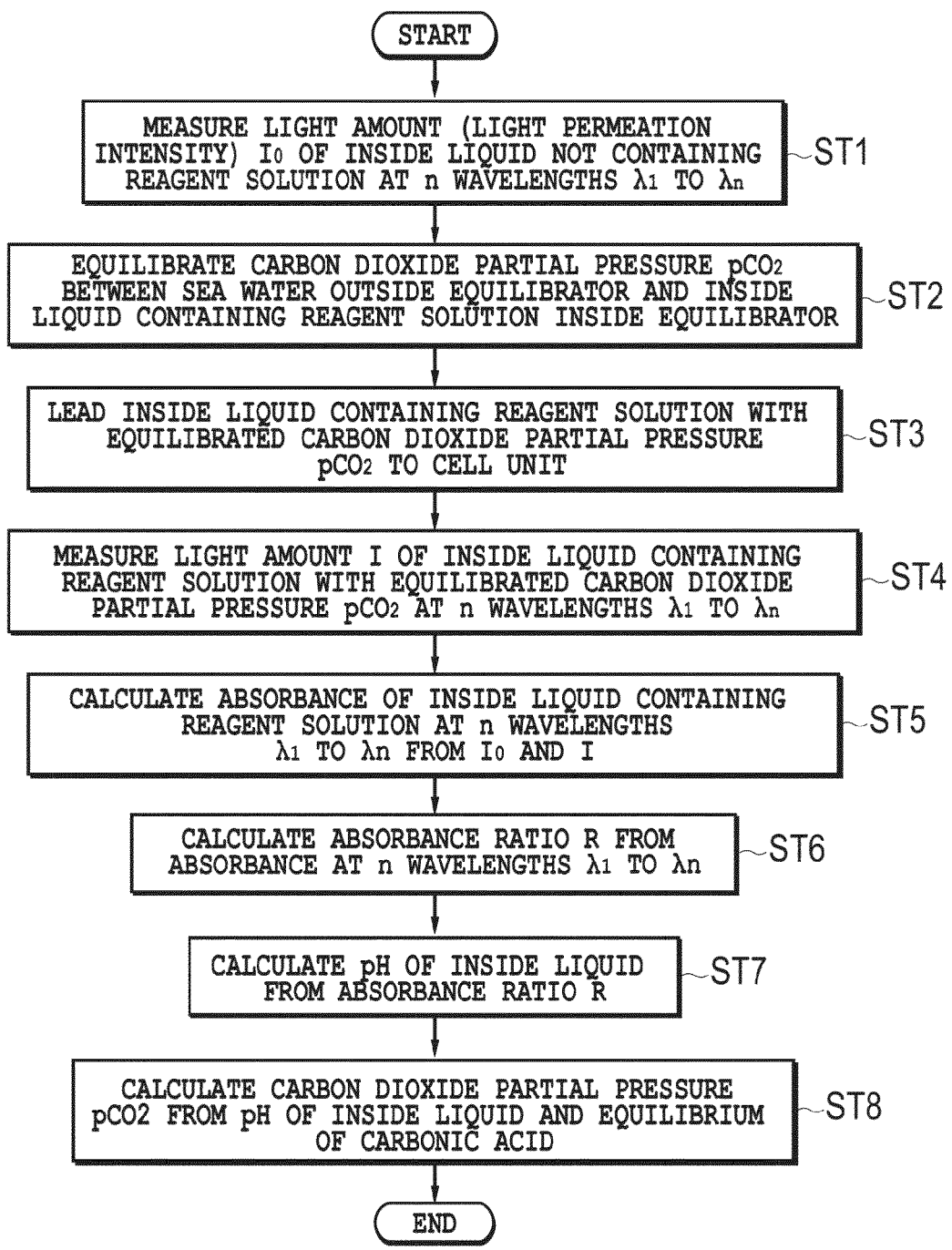
FIG. 3 is a flowchart for computation of the partial pressure of carbon dioxide $pCO_2$ in sea water.

FIG. 3 is a flowchart for a case where the CPU substrate 63 of the apparatus 1 according to the embodiment computes the partial pressure of carbon dioxide $pCO_2$ in sea water.

First, in step ST1, the inside liquid feed pump P1 is driven with only the valves V2 and V4 open to supply the inside liquid, which is pure water stored in the pure water container 7 and having passed through the equilibrator, to the inside flow passage 23 of the body portion 33. Light at n (n is an integer of two or more) wavelengths $\lambda_1$ to $\lambda_n$ determined in advance is irradiated to the inside liquid by the LED unit 59 to measure the light amount (light permeation intensity) $I_0$ of the solution not containing the pH-sensitive colorimetric reagent at the n wavelengths $\lambda_1$ to $\lambda_n$, respectively.

Next, in step ST2, the inside liquid feed pump P1 is driven with only the valves V1 and V4 open to feed the reagent solution charged in the reagent cylinder 5 to the equilibrator 3 to equilibrate the partial pressure of carbon dioxide $pCO_2$ in sea water outside the equilibrator 3 and the partial pressure of carbon dioxide $pCO_2$ in the inside liquid containing the reagent solution inside the equilibrator 3. In order to equilibrate the partial pressure of carbon dioxide $pCO_2$ in sea water outside the equilibrator 3 and the partial pressure of carbon dioxide $pCO_2$ in the inside liquid containing the reagent solution inside the equilibrator 3, the inside liquid not containing the reagent solution may be discharged to the outside from the waste liquid conduit 26, and thereafter the inside liquid containing the reagent solution may be circulated by closing the valve V4 and opening the valve V3.

In step ST3, the inside liquid containing the reagent solution with an equilibrated carbon dioxide partial pressure $pCO_2$ is fed to the cell unit 9. In step ST4, the light amount (light permeation intensity) I of the inside liquid containing the reagent solution with an equilibrated carbon dioxide partial pressure $pCO_2$ at the n wavelengths $\lambda_1$ to $\lambda_n$, respectively, is measured. In step ST5, the absorbance is calculated from the measured light amount $I_0$ and light amount I at each of the n wavelengths $\lambda_1$ to $\lambda_n$. In step ST6, the absorbance ratio R is calculated from the obtained absorbance. In step ST7, the pH of the inside liquid containing the reagent solution is calculated from the absorbance ratio R.

The process from the measurement of the light amount $I_0$ and the light amount I to the calculation of the pH of the inside liquid containing the reagent solution will be described in detail.

[Measurement of Hydrogen Ion Concentration [$H^+$]]

If a sulfonephthalein pH indicator such as bromothymol blue is contained in the inside liquid as the colorimetric indicator (referred to tentatively as "indicator I"), the colorimetric indicator I establishes dissociation equilibriums at two stages indicated by the following formulas (1) and (2) in the inside liquid.

$$H_2I \leftrightarrow HI^- + H^+ \quad (1)$$

$$HI^- \leftrightarrow I^{2-} + H^+ \quad (2)$$

Other examples of the sulfonephthalein pH indicator include bromocresol purple, bromophenol blue, bromothymol blue, metacresol purple, phenol red, and thymol blue.

If the dissociation constant of the indicator $H_2I$ is defined as $K_{(H2I)}$, $K_{(H2I)}$ can be represented by the following formula (3). If the dissociation constant of $HI^-$ of the indicator at the second stage is defined as $K_{(HI)}$, $K_{(HI)}$ can be represented by the following formula (4), and the pH (hydrogen ion concentration index) of sea water can be represented by the formula (5) based on the formula (4). [$H_2I$] indicates the concentration of an undissociated form in the indicator $H_2I$, [$HI^-$] indicates the concentration of a first dissociated form in the indicator $H_2I$, $[I^{2-}]$ indicates the concentration of a second dissociated form in the indicator $H_2I$, and $[H^+]$ indicates the concentration of hydrogen ions.

$$K_{(H2I)} = ([H^+] \cdot [HI^-])/[H_2I] \quad (3)$$

$$K_{(HI)} = ([H^+] \cdot [I^{2-}])/[HI^-] \quad (4)$$

$$pH = pK_{(HI)} + \log([I^{2-}]/[HI^-]) \quad (5)$$

It should be noted that $pH = -\log([H^+])$ and $pK_{(HI)} = -\log(K_{(HI)})$.

The molar absorption coefficients of the first dissociated form ($HI^-$) and the second dissociated form ($I^{2-}$) at the wavelength $\lambda_1$ are defined as $_1\epsilon_{HI}$ and $_1\epsilon_{I-}$, respectively, and the molar absorption coefficients of the first dissociated form ($HI^-$) and the second dissociated form ($I^{2-}$) at the wavelength $\lambda_2$ are defined as $_2\epsilon_{HI}$ and $_2\epsilon_{I-}$, respectively. Then, if the length of the light irradiation portion 23a of the inside flow passage 23 is defined as L, the absorbance $Abs_1$ and $Abs_2$ of the inside liquid at the wavelengths $\lambda_1$ and $\lambda_2$ can be represented by the following formulas (6) and (7), respectively.

$$Abs_1 = {}_1\epsilon_{I-} \cdot L \cdot [I^{2-}] + {}_1\epsilon_{HI} \cdot L \cdot [HI^-] \quad (6)$$

$$Abs_2 = {}_2\epsilon_{I-} \cdot L \cdot [I^{2-}] + {}_2\epsilon_{HI} \cdot L \cdot [HI^-] \quad (7)$$

In the formulas (6) and (7), the ratio of the absorbance $Abs_1$ at the wavelength $\lambda_1$ to the absorbance $Abs_2$ at the wavelength $\lambda_2$ is defined as $R = Abs_1/Abs_2$, and the ratio between the molar absorption coefficients is defined as $e_{1(I)} = {}_1\epsilon_{HI}/{}_2\epsilon_{HI}$, $e_{2(I)} = {}_1\epsilon_{I-}/{}_2\epsilon_{HI}$, and $e_{3(A)} = {}_2\epsilon_{I-}/{}_2\epsilon_{HI}$. Then, the formulas (6) and (7) can be indicated by the following formula (8). That is, the ratio between $[HI^-]$ and $[I^{2-}]$ can be calculated from the absorbance and the molar absorption coefficients at two wavelengths (wavelengths $\lambda_1$ and $\lambda_2$).

$$([I^{2-}]/[HI^-]) = (R - e_{1(I)})/(e_{2(I)} - R \cdot e_{e(I)}) \quad (8)$$

Hence, the following formula (9) can be derived from the formulas (5) and (8).

$$pH = pK_{(HI)} + \log[(R - e_{1(I)})/(e_{2(I)} - R \cdot e_{3(I)})] \quad (9)$$

The value of R can be obtained by measuring the light amount (light permeation intensity) $I_0$ of the solution not containing the colorimetric reagent and the light amount (light permeation intensity) I of the inside liquid containing the solution containing the colorimetric indicator, and calculating the absorbance $Abs = -\log(I/I_0)$.

From what has been described above, $[H^+]$ can be indicated by the following formula (10) having $e_{1(I)}$, $e_{2(I)}$, $e_{3(I)}$, and $K_{(HI)}$ as parameters.

$$[H^+] = F[R, K_{(I)}, e_{1(I)}, e_{2(I)}, e_{3(I)}] \quad (10)$$

$_\lambda\epsilon_{I-}$ and $_\lambda\epsilon_{HI}$ can be experimentally obtained by achieving sufficiently high alkalinity or sufficiently low acidity with respect to $pK_{(HI)}$.

$$_\lambda\epsilon_{I-} = {}_\lambda Abs_1(I^-)/([I^{2-}] \cdot L) \quad (11)$$

$$_\lambda\epsilon_{HI} = {}_\lambda Abs_1(HI)/([HI^-] \cdot L) \quad (12)$$

In this way, if $e_{1(I)}$, $e_{2(I)}$, $e_{3(I)}$, and $K_{(HI)}$ have been obtained in advance, the hydrogen ion concentration $[H^+]$ of the inside liquid can be obtained by measuring R.

[Equilibrium of Carbonic Acid System]

The equilibrium of the carbonic acid system of sea water is described in detail in DOE (1994) Handbook of methods for the analysis of the various parameter of the carbon dioxide system in sea water (Version 2, A. G. Dickson & C. Goyet, eds. ORNL/CDIAC-74), and will be briefly described below.

When carbon dioxide is dissolved in water (formulas (13) and (14)), hydrogen carbonate ions $HCO_3^-(aq)$ and carbonate ions $CO_3^{2-}(aq)$ are generated, and equilibrium reactions indicated by the following formulas (15) and (16) are caused.

$$CO_2(g) \leftrightarrow CO_2(aq) \quad (13)$$

$$CO_2(aq) + H_2O(l) \leftrightarrow H_2CO_3(aq) \quad (14)$$

$$H_2CO_3(aq) \leftrightarrow H^+(aq) + HCO_3^-(aq) \quad (15)$$

$$HCO_3^-(aq) \leftrightarrow H^+(aq) + CO_3^{2-}(aq) \quad (16)$$

It is difficult to discuss $H_2CO_3(aq)$ and $CO_2(aq)$ separately in the formulas (13) to (16). Thus, when the total of $H_2CO_3(aq)$ and $CO_2(aq)$ is expressed as $CO2^*(aq)$, the following formulas (17) and (18) are obtained.

$$CO_2(g) \leftrightarrow CO2^*(aq) \quad (17)$$

$$CO2^*(aq) + H_2O(l) \leftrightarrow H^+(aq) + HCO_3^-(aq) \quad (18)$$

The equilibrium of the formulas (17) and (18) can be indicated by the following formulas (19) to (21) using an equilibrium constant.

$$K_0 = [CO2^*]/f_{(CO2)} \quad (19)$$

$$K_1 = [H^+][HCO_3^-]/[CO_2^*] \quad (20)$$

$$K_2 = [H^+][CO_3^{2-}]/[HCO_3^-] \quad (21)$$

$f_{(CO2)}$ is the fugacity of carbon dioxide. The relationship of $f_{(CO2)}$ with the carbon dioxide partial pressure can be indicated by the following formula (22).

$$f_{(CO2)} = (x(CO_2) \cdot \exp(1/RT) \int (V_{(CO2)} - RT/p')dp' \quad (22)$$

As indicated by the formula (22), when the carbon dioxide partial pressure $pCO_2 = (x(CO_2) \cdot p)$ is measured, the fugacity of carbon dioxide can be calculated from the total pressure of the gas and the salinity of sea water. $x(CO_2)$ is the mole fraction of $CO_2$, and p is the total pressure of the gas phase.

[Calculation of $pCO_2$ from pH of Inside Liquid]

When the hydrogen ion concentration $[H^+]$ of the reagent solution is calculated, the concentration of sodium ions to be added during preparation of the reagent solution is adjusted in advance. An equilibrium of carbonic acid is also established for the reagent solution as for sea water, and the equilibrium constant is a generally known value which is slightly different from that for sea water.

For the inside liquid, the sum of positive ions and the sum of negative ions establish the formula (23) based on the ion balance, and $[H^+]$ is calculated from the measured R.

$$[HCO_3^-] + 2[CO_3^{2-}] + [OH^-] + [HI^-] + 2[I^{2-}] = [H^+] + [Na^+] \quad (23)$$

The concentration of a pigment added in advance is defined as $\Sigma I$. When the pH is 4 or more, $[H_2I]$ is nearly equal to 0, and $[HI^-]$ and $[I^{2-}]$ are indicated by the formulas (24) and (25) based on $\Sigma I = [HI^-] + [I^{2-}]$ and the formula (4).

$$[HI^-] = (\Sigma I)[H^+]/([H^+] + K_{(HI)}) \quad (24)$$

$$[I^{2-}] = (\Sigma I)K_{(HI)}/([H^+] + K_{(HI)}) \quad (25)$$

Further, the dissociation of water is indicated by the formula (26).

$$[OH^-] = Kw/[H^+] \quad (26)$$

The formulas (27) and (28) are derived from the formulas (20) and (21).

$$[HCO_3^-] = [CO_2^*]K_1/[H^+] \quad (27)$$

$$[CO_3^{2-}] = ([CO_2^*]K_1/[H^+])K_2/[H^+] \quad (28)$$

Thus, the formula (29) is derived from the formula (23).

$$[CO_2^*]K_1/[H^+]+2([CO_2^*]K_1/[H^+])K_2/[H^+]+Kw/[H^+]+(\Sigma I)[H^+]/([H^+]+K_{(HI)}+2(\Sigma I)K_{(HI)}/([H^+]+K_{(HI)})=[H^+]+[Na^+] \quad (29)$$

$[CO_2^*]$ can be calculated by introducing the concentration of the indicator added in advance into $(\Sigma I)$, the concentration of the alkali added in advance into $[Na^+]$, the concentration calculated from R into $[H+]$, and the dissociation constant into the others in the formula (29).

$f_{(CO2)}$ is calculated from the formula (19) based on the obtained $[CO_2^*]$. $x(CO_2)$ is calculated based on the obtained $f_{(CO2)}$ and the formula (22). Further, the inside $pCO_{2(IN)}$ is calculated based on the total pressure (atmospheric pressure) of the gas phase (atmosphere). If $pCO_{2(IN)}$ of the inside liquid and $pCO_{2(SEA)}$ of sea water has reached an equilibrium via the gas permeable membrane, $pCO_{2(IN)}=pCO_{2(SEA)}$ is established. In the embodiment, the pH of the inside liquid is adjusted to 5.5 to 6.0 by shifting the entire system by varying $[Na^+]$ in the formula (29).

Figure 4:
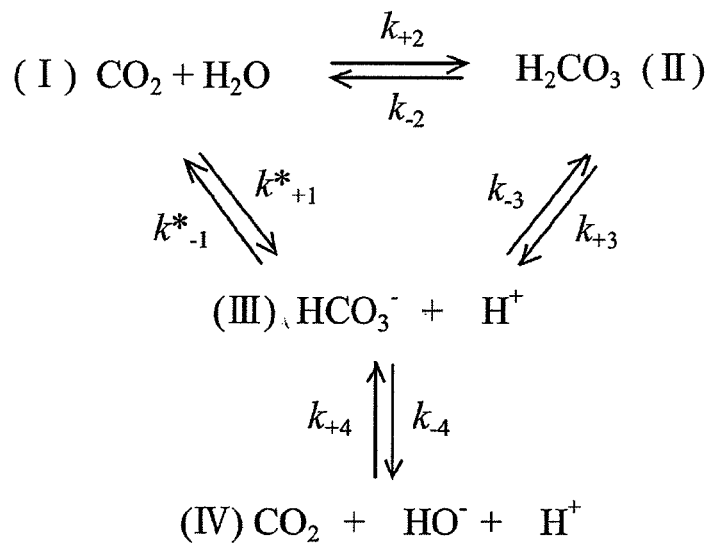
FIG. 4 illustrates the mechanism of a reaction that occurs when carbon dioxide is dissolved into water to be dissociated.

Next, the relationship between the speed at which carbon dioxide is dissolved into water and the pH will be briefly described with reference to FIG. 4. FIG. 4 illustrates an equilibrium state established when carbon dioxide is dissolved in water. The reaction in which $CO_2$ is turned from a hydrated state into carbonic acid, that is, the reaction from the state (I) into the state (II), is significantly slow, and the reaction from the state (II) into the state (III) is faster. The concentration of $H_2CO_3$ is known to be 0.3% or less with respect to $CO_2$. The rate of reaction significantly varies according to the temperature and the pH, and is low when the temperature is low and when the pH is around neutral. For details, see Johnson K. S., Carbon dioxide hydration and dehydration kinetics in seawater (Limnol Oceanogr., 27(5), 1982, 849-855). The rate of reaction in which $CO_2$ is turned from a hydrated state into carbonic acid is calculated using the formula (30).

$$1/\tau=(k_{+1}+k_{-1}[H^+]+k_{+4}+k_{-4}[OH^-]) \quad (30)$$

Figure 5:
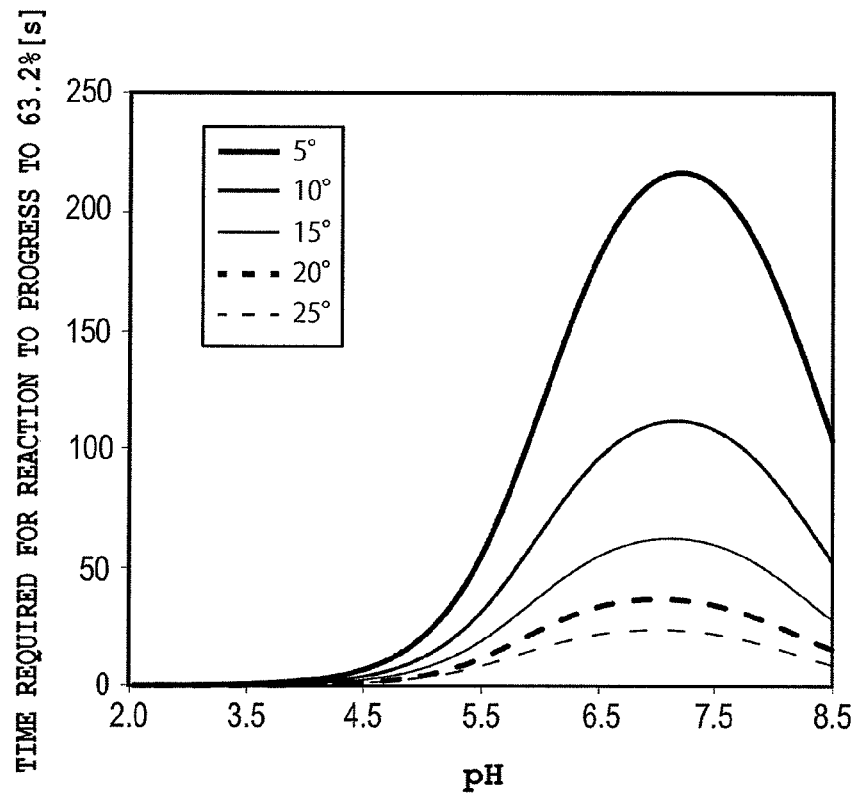
FIG. 5 is a graph illustrating the pH value and the time required for $CO_2$ to be hydrated to reach an equilibrium of carbonic acid of 63.2%.

FIG. 5 is a graph illustrating the pH value and the time required for $CO_2$ to be hydrated to reach an equilibrium of carbonic acid of 63.2%. When the pH is 5 or less, the response is significantly quick. However, the dissociation occurs to reduce the amount of generated hydrogen carbonate ions, and thus the pH is not significantly varied. Therefore, the pH is considered to be optimum at 5 to 6, preferably around 5.5 to 6, at which both the response rate and the amount of variation in pH are good.

Figure 6:
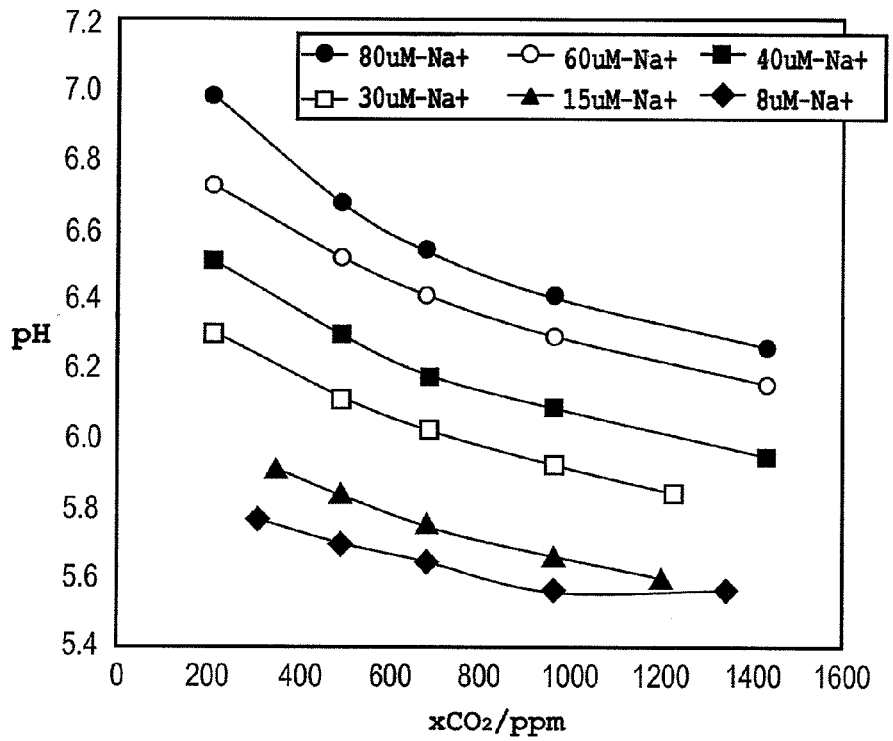
FIG. 6 is a graph in which the pH of an inside liquid is plotted with the carbon dioxide partial pressure varied and with the sodium concentration of the inside liquid varied.

FIG. 6 is a graph in which the pH of the inside liquid is plotted with the carbon dioxide partial pressure varied and with the sodium concentration of the inside liquid varied. The pH of the inside liquid is taken when the temperature of the inside liquid is 25° C. Sodium has been added in the form of NaOH, $NaHCO_3$, or $Na_2CO_3$. When the sodium concentration is 30 μM or more, the pH value is 6.0 or more. When the sodium concentration is 8 μM, the pH is 5.8 or less, but the output cannot be captured well when the concentration of $xCO_2$ is high. The sodium concentration is optimum at 15 μM, at which variations in output can be captured even when the concentration of $xCO_2$ is high.

Figure 7:
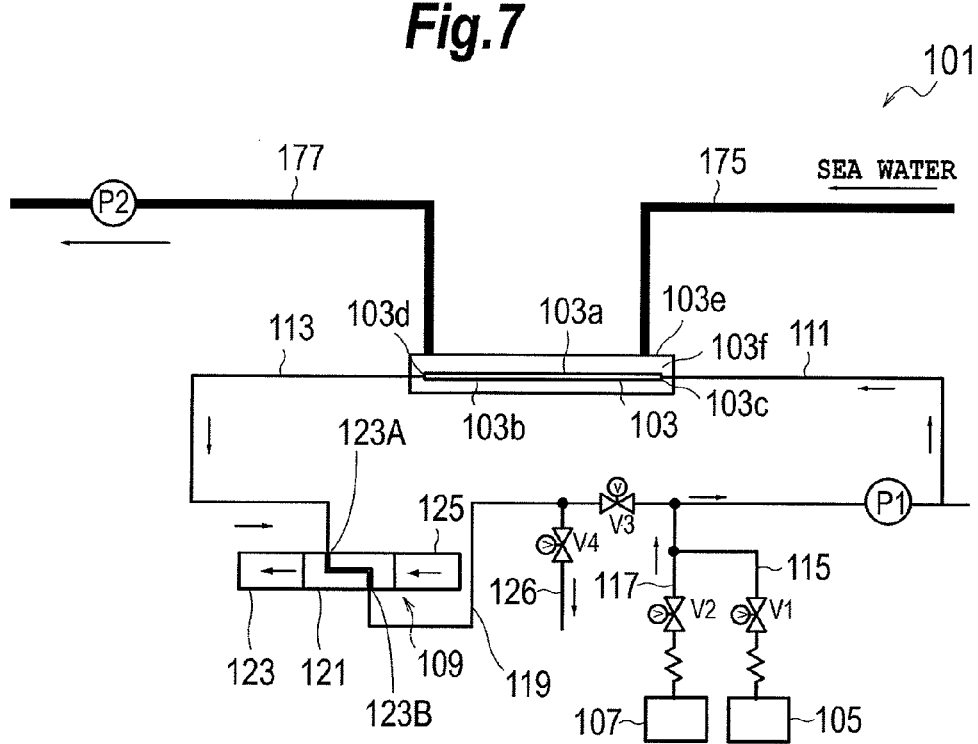
FIG. 7 schematically illustrates the configuration of an apparatus for measuring the partial pressure of carbon dioxide according to a second embodiment of the present invention.

FIG. 7 schematically illustrates the configuration of an apparatus for measuring the partial pressure of carbon dioxide 101 according to a second embodiment of the present invention. In FIG. 7, component parts that are similar to those illustrated in FIG. 1 are denoted by reference numerals obtained by adding 100 to the reference numerals affixed to their counterparts in FIG. 1 to omit detailed description. An equilibrator 103 according to the embodiment has a double tube structure including a tubular member 103a formed from a tubular gas permeable membrane and a hollow cylindrical outer tubular member 103e with an inside diameter of 6 mm provided outside the tubular member 103a and formed from polytetrafluoroethylene, and includes a sea water flow passage 103f provided between the tubular member 103a and the outer tubular member 103e. The outer tubular member 103e is connected to a sea water introduction passage 175 configured to introduce sea water into the sea water flow passage 103f and a sea water discharge passage 177 configured to discharge the sea water introduced into the sea water flow passage 103f. The sea water discharge passage 177 is provided with a sampling pump P2 configured to sample seawater from under the sea. The sampling pump P2 includes a pump drive device (not illustrated).

With the apparatus 101 according to the embodiment, an inflow of sea water into the sea water flow passage 103f of the equilibrator 103 can be stopped by controlling drive of the sampling pump P2. Therefore, sea water with a high carbon dioxide partial pressure can be caused to reside in the sea water flow passage 103f by stopping drive of the sampling pump P2 when the apparatus 1 passes through a sea area with a high carbon dioxide partial pressure together with the AUV, for example. Therefore, the partial pressure of carbon dioxide $pCO_2$ in the residing sea water and the partial pressure of carbon dioxide $pCO_2$ in the inside liquid can be sufficiently equilibrated, which makes it possible to measure the carbon dioxide partial pressure with high accuracy.

When the apparatus 101 is mounted inside the AUV, for example, sea water resides in the AUV, and the carbon dioxide partial pressure may not be accurately measured because sea water with a high carbon dioxide partial pressure does not reach a location around the equilibrator 103 unless the sampling pump P2 is provided. If the sampling pump P2 is provided, however, sea water with a high carbon dioxide partial pressure can be positively caused to flow into the sea water flow passage 103f, which makes it possible to accurately measure the carbon dioxide partial pressure.

Figure 8:
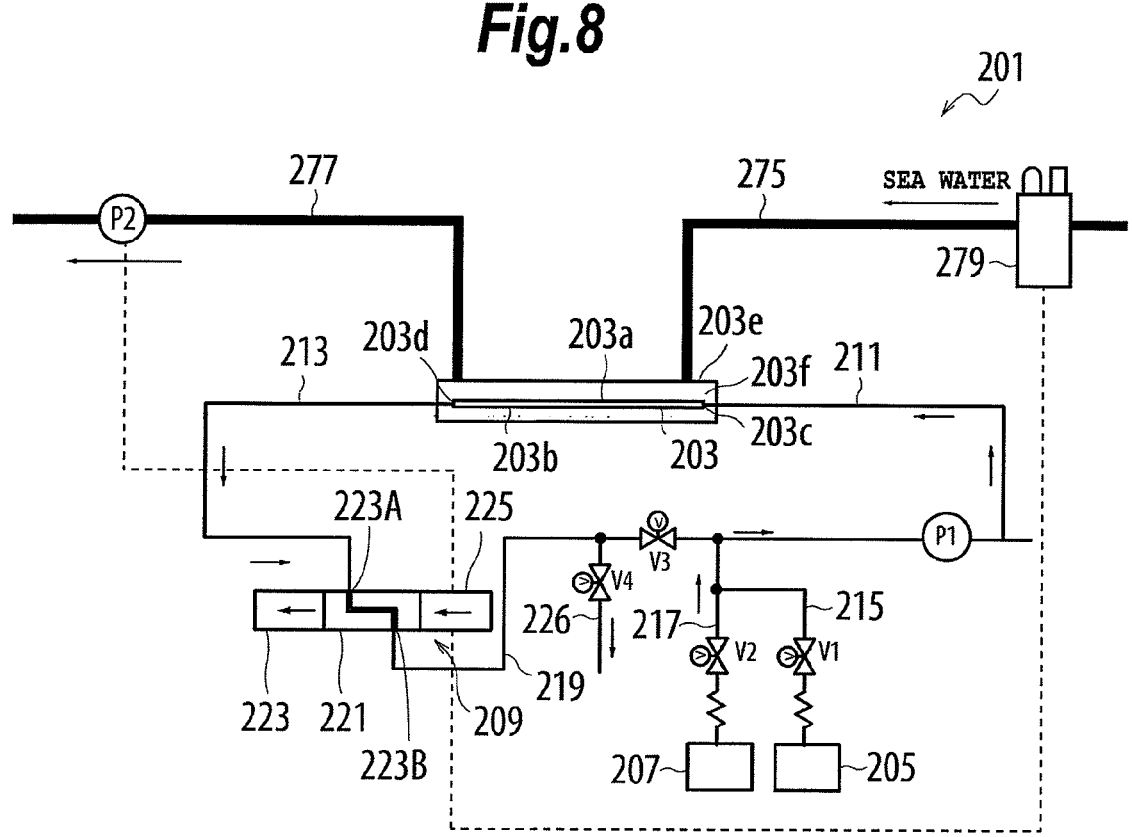
FIG. 8 schematically illustrates the configuration of an apparatus for measuring the partial pressure of carbon dioxide according to a third embodiment of the present invention.
Figure 9:
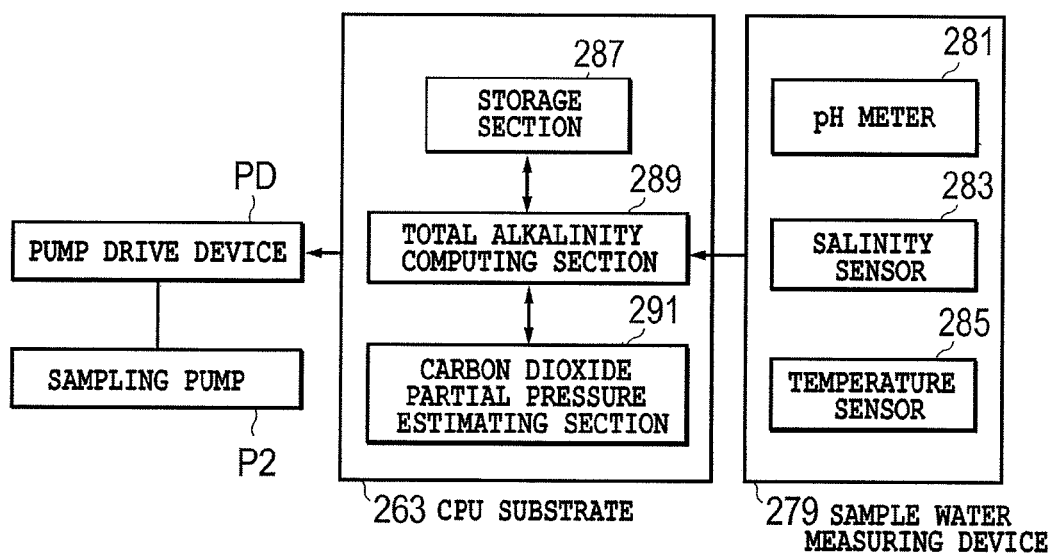
FIG. 9 is a block diagram illustrating the configuration of a part of a signal processing device formed inside the apparatus according to the third embodiment.

FIG. 8 schematically illustrates the configuration of an apparatus for measuring the partial pressure of carbon dioxide 201 according to a third embodiment of the present invention. FIG. 9 is a block diagram illustrating the configuration of a part of a signal processing device formed inside the apparatus 201 according to the third embodiment. In FIGS. 8 and 9, component parts that are similar to those shown in FIG. 1 are denoted by reference numerals obtained by adding 200 to the reference numerals affixed to their counterparts in FIG. 1 to omit detailed description. In the embodiment, as in the second embodiment, an equilibrator 203 has a double tube structure including an outer tubular member 203e, and includes a sea water flow passage 203f. The apparatus 201 includes a seawater introduction passage 275, a sea water discharge passage 277, and the sampling pump P2. In the embodiment, in particular, the apparatus 2 includes a sample water measuring device 279. The sample water measuring device 279 includes at least a pH meter 281 configured to measure the pH of sample water, a salinity sensor 283 configured to measure the salinity of the sample water, and a temperature sensor 285 configured to measure the temperature of the sample water. The sample water measuring device 279 is electrically connected to a CPU substrate 263 in a light source unit 225, and outputs various measurement results to the CPU substrate 263. The CPU substrate 263 is electrically connected to a pump drive device PD for the sampling pump P2, and outputs a control signal for controlling drive of the sampling pump P2 to the pump drive device PD. When the pH meter 281 measures a pH value that is equal to or more than a prescribed pH value, the pump drive device PD stops drive of the sampling pump P2 until the apparatus 201 completes the measurement. The CPU substrate 263 includes a storage section 287, a total alkalinity computing section 289, and a carbon dioxide partial pressure estimating section 291.

The relationship among the total carbonic acid concentration $C_T$, the total alkalinity $A_T$, and the carbonate alkalinity $A_C$ of sea water will be described.

The total carbonic acid concentration $C_T$ of sea water is defined by the following formula (31).

$$C_T = [CO_{2*}] + [HCO_3^-] + [CO_3^{2-}] \quad (31)$$

Further, the total alkalinity $A_T$ of sea water is defined as the difference between the proton donor and the proton acceptor as indicated by the following formula (32). Components omitted from the formula (32) are minute enough to ignore.

$$A_T = [HCO_3^-] + 2[CO_3^{2-}] + [B(OH)_4^-] + [OH^-] + [HPO_4^{2-}] + 2[PO_4^{3-}] + [SiO(OH)_3^-] + [NH_3] + [HS^-] + \ldots - [H^+]_F - [HSO_4^-] - [HF] - [H_3PO_4] - \quad (32)$$

In addition, the carbonate alkalinity $A_C$ can be indicated by the following formula (33).

$$A_C = [HCO_3^-] + 2[CO_3^{2-}] \quad (33)$$

The relationship between the total alkalinity $A_T$ and the carbonate alkalinity $A_C$ can be indicated by the following formula (34). Components omitted from the formula (34) are minute enough to ignore.

$$A_C = A_T - ([B(OH)_4^-] + [OH^-] + [HPO_4^{2-}] + 2[PO_4^{3-}] + [SiO(OH)_3^-] + [NH_3] + [HS^-] + \ldots - [H^+]F - [HSO_4^-] - [HF] - [H_3PO_4] -) \quad (34)$$

$([B(OH)_4^-] + [OH^-] + [HPO_4^{2-}] + 2[PO_4^{3-}] + [SiO(OH)_3^-] + [NH_3] + [HS^-] + \ldots [H^+]F - [HSO_4^-] - [HF] - [H_3PO_4]-)$ can be estimated from the salinity.

$A_C$ can be calculated from the salinity and $A_T$. The formulas (35) to (37) can be derived from the formulas (20), (21), and (33).

$$[HCO_3^-] = [CO_2^*]K_1/[H^+] \quad (35)$$

$$[CO_3^{2-}] = ([CO_2^*]K_1/[H^+])K_2/[H^+] \quad (36)$$

$$[CO_2^*] = A_C[H^+]^2/(K_1[H^+] + 2K_2) \quad (37)$$

Next, the total alkalinity will be described. The total alkalinity ($NA_T = A_T*35/S$) standardized to the salinity (S=35) is known to be 2300 to 2350 µmol/kg for surface-layer oceanic water, about 2300 µmol/kg for the Atlantic Ocean, and around 2350 µmol/kg for the Pacific Ocean. The total alkalinity is often higher for deep water, and occasionally reaches 2450 µmol/kg. As a matter of course, the total alkalinity varies for offshore water and in sea areas in which calcification occurs such as a coral reef. A method of roughly calculating $A_T$ from the salinity and $NA_T$ is known. For a see area in which $NA_T$ does not significantly vary, $A_C$ is calculated from $A_T$ roughly calculated from $NA_T$ using the formula (34). Then, $[CO_2^*]$ is calculated using the formula (33) using the measured pH, $f(CO_2)$ is calculated using the formula (19), $x(CO_2)$ is calculated using the formula (22), and $pCO_2$ is calculated from the total pressure (atmospheric pressure) of the gas phase (atmosphere).

Specific $NA_T$ is calculated using an expression or the like corresponding to the sea area of each ocean as illustrated in FIG. 8, for example. (Source: Millero, F. J., Lee, K., Roche, M., 1998. Distribution of alkalinity in the surface water of the major ocean (Mar. Chem. 60, 111-130))

The storage section 287 according to the embodiment stores expressions for calculating $NA_T$ illustrated in FIG. 8. The total alkalinity computing section 289 computes the total alkalinity based on the measurement result from the salinity sensor 283, the measurement result from the temperature sensor 285, and the calculation expression stored in the storage section 293, and outputs the computed total alkalinity to the carbon dioxide partial pressure estimating section 291. The carbon dioxide partial pressure estimating section 291 computes an expected value of the partial pressure of carbon dioxide in sea water based on the total alkalinity and the pH of sea water measured by the pH meter 281. Information on the computed carbon dioxide partial pressure is output to the pump drive device PD together with information on the pH of sea water. The pump drive device PD drives the pump P2 based on information on the pH of sea water and information on the computed carbon dioxide partial pressure.

Figure 11:
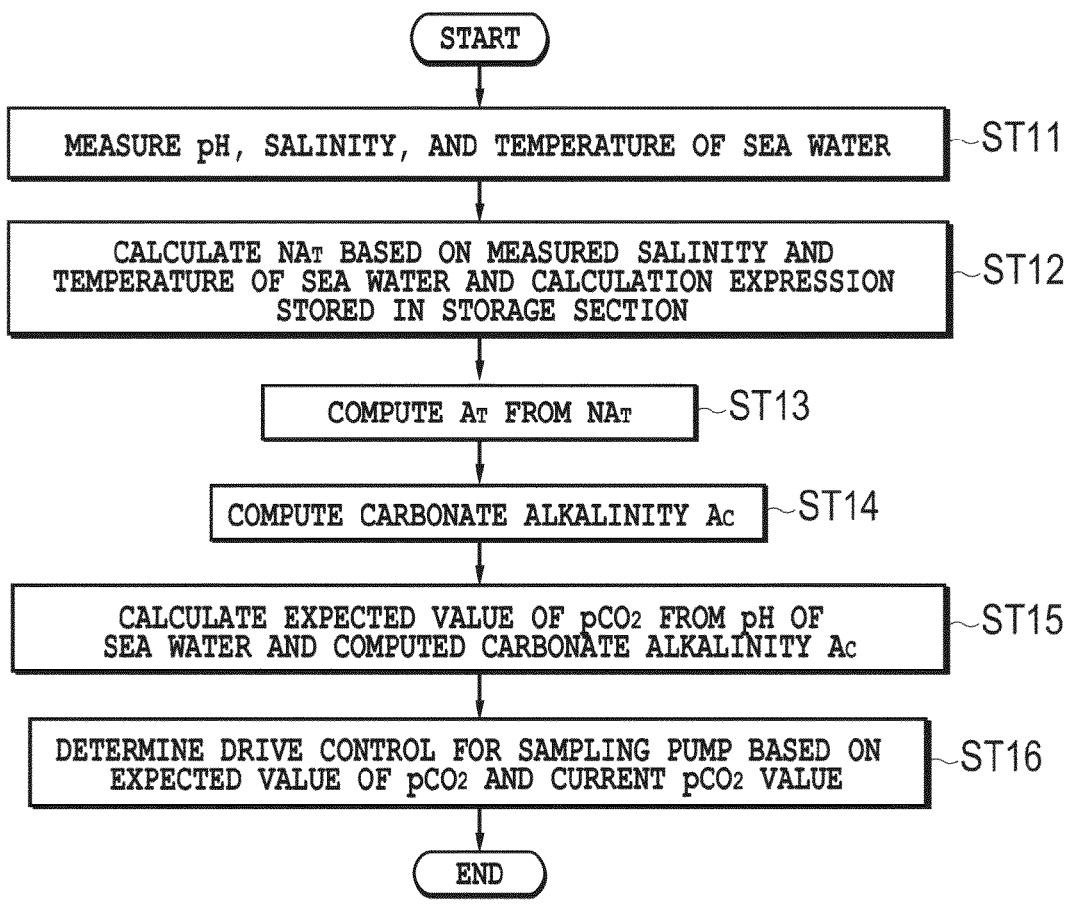
FIG. 11 is a flowchart for estimation of the partial pressure of carbon dioxide $pCO_2$ from the pH and the total alkalinity.

FIG. 11 is a flowchart for estimating the partial pressure of carbon dioxide $pCO_2$ from the pH and the total alkalinity to control drive of the pump. First, in step ST11, the pH meter 281, the salinity sensor 283, and the temperature sensor 285 which measures the temperature of sample water measure the pH, the salinity, and the temperature pH of sea water. In step ST12, the total alkalinity computing section 289 calculates $NA_T$ based on the salinity and the temperature of sea water measured in step ST12 and the calculation expression stores in the storage section 293. Next, in step ST13, the total alkalinity computing section 289 computes $A_T$ from $NA_T$. In step ST14, the carbon dioxide partial pressure estimating section 291 computes the carbonate alkalinity $A_C$. Next, in step ST15, the carbon dioxide partial pressure estimating section 291 calculates an expected value of $pCO_2$ from the pH of sea water measured in step ST11 and the computed carbonate alkalinity $A_C$. Further, in step ST16, a control signal for controlling drive of the sampling pump P2 is generated based on the expected value of $pCO_2$ and the current $pCO_2$ value, and transmitted to the pump drive device PD. The pump drive device PD controls drive of the sampling pump P2 based on the control signal.

In the embodiments described above, the partial pressure of carbon dioxide in deep sea is measured. As a matter of course, however, the apparatus may be disposed at any location under the sea to measure the carbon dioxide partial pressure. As a matter of course, in addition, the apparatus may be utilized to measure the partial pressure of carbon dioxide in fresh water in a lake or the like and brackish water.

In the embodiments described above, in addition, BCP is utilized as the colorimetric indicator. However, other pH-sensitive colorimetric reagents may also be used. Alternatively, reagent solutions other than the pH-sensitive colorimetric reagents may also be used.

In the embodiments described above, further, the inside flow passage has a cranked shape. However, the inside flow passage may have a different shape such as a U shape and an H shape.

INDUSTRIAL APPLICABILITY

According to the present invention, the lead wire used to electrically connect between the light source unit and the light receiving element unit is not exposed to water in which the apparatus for measuring the partial pressure of carbon dioxide is disposed. Thus, the apparatus is hardly broken because of a bad connection or the like. Moreover, it is possible to reduce the number of locations at which a watertight structure is to be adopted. In addition, the flow cell and the first container and the second container having a watertight structure are watertightly attached to each other. Thus, water around the apparatus does not enter the apparatus. Therefore, the lead wire and a light conducting passage that transmits light are not affected by, the water pressure of water in which the apparatus is disposed. Thus, a signal transferred between the light source unit and the light receiving element unit is not affected by the water pressure, and a measurement error of the carbon dioxide partial pressure or the like is not caused. Hence, according to the present invention, the carbon dioxide partial pressure can be accurately measured even if the apparatus is disposed in deep sea in which the water pressure is high, for example.

DESCRIPTION OF REFERENCE NUMERALS 1 apparatus for measuring partial pressure of carbon dioxide
3 equilibrator
3a tubular member
3b inside liquid flow passage
3c one end portion
3d other end portion
5 reagent cylinder
7 pure water cylinder
9 cell unit
11 first liquid feed conduit
13 second liquid feed conduit
15 third liquid feed conduit
17 fourth liquid feed conduit
19 fifth liquid feed conduit
21 flow cell
23 inside flow passage
23a light irradiation portion
23b introduction passage portion
23c discharge passage portion
23d opening portion
23e opening portion
23f inlet port
23g outlet port
26 waste liquid conduit
27 light source unit
29 light receiving element unit
33 flow cell body
33a, 33b stepped portion
33c through hole
35 light source pressure-proof lens
37 light receiving element pressure-proof lens
39 first outer wall surface
39a recessed portion
41 second outer wall surface
41a recessed portion
43 peripheral wall surface
P1 inside liquid feed pump
V1 to V4 valve

The invention claimed is:

1. An apparatus for measuring the partial pressure of carbon dioxide, the apparatus being disposed underwater and comprising:
an equilibrator including a solution flow passage, a reagent solution, and a gas permeable membrane that allows permeation of carbon dioxide but that does not allow permeation of the reagent solution, the reagent solution flows through the solution flow passage, the reagent solution having an absorbance varying with the partial pressure of carbon dioxide, the equilibrator being configured to equilibrate the partial pressure of carbon dioxide in the reagent solution and the partial pressure of carbon dioxide in sample water;
a liquid feed pump configured to feed the reagent solution to the solution flow passage;
a flow cell having a body portion formed with an inside flow passage through which the reagent solution flowing out of the solution flow passage of the equilibrator flows;
a light source unit including a light source configured to irradiate light to the inside flow passage;
a light receiving element unit including a light receiving element configured to receive the light having passed through the inside flow passage; and
a carbon dioxide partial pressure measuring section configured to calculate an absorbance based on an output from the light receiving element unit and to measure the partial pressure of carbon dioxide in the sample water based on the absorbance, wherein:
the body portion of the flow cell has a watertight structure in which the inside flow passage includes a first opening portion watertightly blocked by a first optical window and a second opening portion located opposite to the first opening portion and watertightly blocked by a second optical window;
the light source unit includes a watertight first container watertightly attached to the body portion of the flow cell, the light source unit being configured to irradiate the light from the light source to the inside flow passage through the first optical window;
the light receiving element unit includes a watertight second container watertightly attached to the body portion of the flow cell, the light receiving element unit being configured such that the light receiving element receives the light having passed through the inside flow passage through the second optical window; and
the body portion of the flow cell is formed with an electrical connection member guide passage with an electrical connection member received therein, said electrical connection member being a lead wire used for electrical connection between the light source unit and the light receiving element unit.

2. The apparatus for measuring the partial pressure of carbon dioxide according to claim 1, further comprising:
a sampling pump configured to sample the sample water from the underwater; and
a pump drive device configured to control drive of the sampling pump, wherein
the equilibrator further includes a sample water flow passage through which the sample water passes.

3. The apparatus for measuring the partial pressure of carbon dioxide according to claim 2, further comprising:
a pH meter configured to measure the pH of the sample water, wherein
the pump drive device stops drive of the sampling pump until the carbon dioxide partial pressure measuring section completes the measurement when the pH meter measures a pH value that is equal to or more than a prescribed pH value.

4. The apparatus for measuring the partial pressure of carbon dioxide according to claim 3, further comprising:
a salinity sensor configured to measure the salinity of the sample water;
a temperature sensor configured to measure the temperature of the sample water;

a total alkalinity computing section configured to compute a total alkalinity based on the salinity and the temperature; and a carbon dioxide partial pressure estimating section configured to compute the partial pressure of carbon dioxide based on the total alkalinity and the pH value of the sample water, wherein the pump drive device drives the sampling pump based on the partial pressure of carbon dioxide computed by the carbon dioxide partial pressure estimating section.

5. The apparatus for measuring the partial pressure of carbon dioxide according to claim 3, wherein:

the body portion of the flow cell includes an inlet port constituted by one end of the inside flow passage and an outlet port constituted by the other end of the inside flow passage;

the inlet port and the outlet port are formed in a pair of opposed outer wall surfaces of the body portion, respectively; and the light source unit and the light receiving element unit are attached to the body portion at another different pair of outer wall surfaces of the body portion that serve as attachment surfaces.

6. The apparatus for measuring the partial pressure of carbon dioxide according to claim 5, wherein the reagent solution is a pH-sensitive colorimetric reagent having a pH of 5.5 to 6.

7. The apparatus for measuring the partial pressure of carbon dioxide according to claim 6, wherein the pH-sensitive colorimetric reagent is a sulfonephthalein pH indicator.

8. The apparatus for measuring the partial pressure of carbon dioxide according to claim 3, wherein the reagent solution is a pH-sensitive colorimetric reagent having a pH of 5.5 to 6.

9. The apparatus for measuring the partial pressure of carbon dioxide according to claim 8, wherein the pH-sensitive colorimetric reagent is a sulfonephthalein pH indicator.

10. The apparatus for measuring the partial pressure of carbon dioxide according to claim 2, wherein:

the body portion of the flow cell includes an inlet port constituted by one end of the inside flow passage and an outlet port constituted by the other end of the inside flow passage;

the inlet port and the outlet port are formed in a pair of opposed outer wall surfaces of the body portion, respectively; and the light source unit and the light receiving element unit are attached to the body portion at another different pair of outer wall surfaces of the body portion that serve as attachment surfaces.

11. The apparatus for measuring the partial pressure of carbon dioxide according to claim 10, wherein the reagent solution is a pH-sensitive colorimetric reagent having a pH of 5.5 to 6.

12. The apparatus for measuring the partial pressure of carbon dioxide according to claim 11, wherein the pH-sensitive colorimetric reagent is a sulfonephthalein pH indicator.

13. The apparatus for measuring the partial pressure of carbon dioxide according to claim 2, wherein the reagent solution is a pH-sensitive colorimetric reagent having a pH of 5.5 to 6.

14. The apparatus for measuring the partial pressure of carbon dioxide according to claim 13, wherein the pH-sensitive colorimetric reagent is a sulfonephthalein pH indicator.

15. The apparatus for measuring the partial pressure of carbon dioxide according to claim 1, wherein:

the body portion of the flow cell includes an inlet port constituted by one end of the inside flow passage and an outlet port constituted by the other end of the inside flow passage;

the inlet port and the outlet port are formed in a pair of opposed outer wall surfaces of the body portion, respectively; and the light source unit and the light receiving element unit are attached to the body portion at another different pair of outer wall surfaces of the body portion that serve as attachment surfaces.

16. The apparatus for measuring the partial pressure of carbon dioxide according to claim 15, wherein the reagent solution is a pH-sensitive colorimetric reagent having a pH of 5.5 to 6.

17. The apparatus for measuring the partial pressure of carbon dioxide according to claim 16, wherein the pH-sensitive colorimetric reagent is a sulfonephthalein pH indicator.

18. The apparatus for measuring the partial pressure of carbon dioxide according to claim 1, wherein the reagent solution is a pH-sensitive colorimetric reagent having a pH of 5.5 to 6.

19. The apparatus for measuring the partial pressure of carbon dioxide according to claim 18, wherein the pH-sensitive colorimetric reagent is a sulfonephthalein pH indicator.

20. The apparatus for measuring the partial pressure of carbon dioxide according to claim 1, wherein the flow cell, the watertight first container, and the watertight second container have a pressure-proof structure.

21. A cell unit for an apparatus for measuring the partial pressure of carbon dioxide, comprising:

a watertight flow cell having a body portion formed with an inside flow passage and a reagent solution, the reagent solution flows out of a solution flow passage of an equilibrator, the reagent solution having an absorbance varying with the partial pressure of carbon dioxide;

a light source unit including a light source configured to irradiate light to the inside flow passage, and a watertight first container watertightly attached to the body portion of the flow cell;

a light receiving element unit including a light receiving element configured to receive the light having passed through the inside flow passage, and a watertight second container watertightly attached to the body portion of the flow cell; and a carbon dioxide partial pressure measuring section configured to calculate an absorbance based on an output from the light receiving element unit and to measure the partial pressure of carbon dioxide in the sample water based on the absorbance, wherein:

the body portion of the flow cell has a watertight structure including a first opening portion watertightly blocked by a first optical window and a second opening portion located opposite to the first opening portion and watertightly blocked by a second optical window;

the light source unit is configured to irradiate the light from the light source to the inside flow passage through the first optical window;

the light receiving element unit is configured such that the light receiving element receives the light having passed through the inside flow passage through the second optical window; and the body portion of the flow cell is formed with an electrical connection member guide passage with an electrical connection member received therein, said electrical connection member being a lead wire used for electrical connection between the light source unit and the light receiving element unit.

* * * * *